US012101602B2

(12) United States Patent
Van den Heuvel et al.

(10) Patent No.: US 12,101,602 B2
(45) Date of Patent: *Sep. 24, 2024

(54) IMPLANTABLE SOUND SENSORS WITH NON-UNIFORM DIAPHRAGMS

(71) Applicant: Cochlear Limited, Macquarie University (AU)

(72) Inventors: Koen Erik Van den Heuvel, Hove (BE); Jan Vermeiren, Boechout (BE); Rishubh Verma, Oatley (AU); Antonin Rambault, Mechelen (BE)

(73) Assignee: Cochlear Limited, Macquarie University (AU)

( * ) Notice: Subject to any disclaimer, the term of this patent is extended or adjusted under 35 U.S.C. 154(b) by 70 days.

This patent is subject to a terminal disclaimer.

(21) Appl. No.: 18/070,928

(22) Filed: Nov. 29, 2022

(65) Prior Publication Data

US 2023/0156415 A1      May 18, 2023

Related U.S. Application Data

(63) Continuation of application No. 17/261,229, filed as application No. PCT/IB2019/058791 on Oct. 15, 2019, now Pat. No. 11,553,290.

(60) Provisional application No. 62/749,702, filed on Oct. 24, 2018.

(51) Int. Cl.
*H04R 25/00* (2006.01)
*A61N 1/36* (2006.01)

(52) U.S. Cl.
CPC ......... *H04R 25/604* (2013.01); *H04R 25/609* (2019.05); *H04R 25/65* (2013.01); *A61N 1/36038* (2017.08); *A61N 1/36128* (2013.01); *H04R 2225/67* (2013.01)

(58) Field of Classification Search
CPC . H04R 25/604; H04R 25/609; H04R 2225/67
See application file for complete search history.

(56) References Cited

U.S. PATENT DOCUMENTS

| 4,532,383 A | 7/1985 | Willy |
| 7,322,930 B2 | 1/2008 | Jaeger et al. |
| 9,533,143 B2 | 1/2017 | Van Den Heuvel |
| 2007/0058825 A1* | 3/2007 | Suzuki ................. H04R 19/005 381/174 |

(Continued)

FOREIGN PATENT DOCUMENTS

| CN | 102105192 A | 6/2011 |
| CN | 102598712 A | 7/2012 |

(Continued)

OTHER PUBLICATIONS

International Search Report and the Written Opinion PCT/IB2019/058791, Jan. 17, 2020, 10 pages.

*Primary Examiner* — Sunita Joshi
(74) *Attorney, Agent, or Firm* — Edell, Shapiro & Finnan, LLC

(57) ABSTRACT

Presented herein are implantable sound sensors that include a non-uniform diaphragm mechanically coupled to a vibrating structure of a recipient's middle or inner ear. The non-uniform diaphragm includes a central region and a peripheral region, where the thickness of the central region is greater than the thickness of the peripheral region.

18 Claims, 11 Drawing Sheets

(56) References Cited

U.S. PATENT DOCUMENTS

2013/0116497 A1* 5/2013 Vermeiren ........... H04R 25/606
600/25
2015/0104048 A1 4/2015 Uchida et al.

FOREIGN PATENT DOCUMENTS

| JP | 2004147286 A | 5/2004 |
| KR | 100592100 B1 | 6/2006 |
| KR | 100676401 B1 | 1/2007 |

* cited by examiner

IMPLANTABLE SOUND SENSORS WITH NON-UNIFORM DIAPHRAGMS

BACKGROUND

Field of the Invention

The present invention generally relates to implantable sound sensors for implantable hearing prostheses.

Related Art

Hearing loss is a type of sensory impairment that is generally of two types, namely conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

SUMMARY

In one aspect, a sound sensor implantable in a recipient of a hearing prosthesis is provided. The sound sensor comprises: a biocompatible housing comprising a cavity having an opening at a first end of the housing; a non-uniform diaphragm attached to the housing so as to hermetically seal the opening; a coupling member configured to mechanically couple the non-uniform diaphragm to a vibrating structure of the recipient's middle or inner ear such that the non-uniform diaphragm vibrates in response to vibration of the vibrating structure; and a vibrational sensor disposed in the housing and configured to detect vibration of the non-uniform diaphragm and generate signals representative of the detected vibrations.

In another aspect, an implantable sound sensor is provided. The implantable sound sensor comprises: a biocompatible housing; a diaphragm attached to the housing, wherein the diaphragm comprises at least a first section and a second section having a thickness that is less than a thickness of the first section, wherein the diaphragm is mechanically coupled to a vibrating structure of the recipient's middle or inner so as to vibrate in response to vibration of the vibrating structure; and a vibrational sensor disposed in the housing and configured to detect vibration of the diaphragm and generate signals representative of the detected vibrations.

In another aspect, a sound sensor implantable in a recipient of a hearing prosthesis is provided. The sound sensor comprises: a biocompatible housing comprising an opening; a diaphragm positioned at the opening, wherein the diaphragm comprises a first thickness at a geometric center thereof that is greater than a thickness at a periphery of the diaphragm; a coupling member configured to mechanically couple the diaphragm to a vibrating structure of the recipient's middle or inner ear such that the diaphragm vibrates in response to vibration of the vibrating structure; and a vibrational sensor disposed in the housing and configured to detect vibration of the diaphragm and generate signals representative of the detected vibrations,

BRIEF DESCRIPTION OF THE DRAWINGS

Embodiments of the present invention are described herein in conjunction with the accompanying drawings, in which.

DETAILED DESCRIPTION

Presented herein are implantable sound sensors that include a diaphragm mechanically coupled to a vibrating structure of a recipient's middle or inner ear. The diaphragm includes a central region and a peripheral region, where the thickness of the central region is greater than the thickness of the peripheral region.

Embodiments of the present invention are described herein primarily in connection with one type of implantable hearing prosthesis, namely a totally or fully implantable cochlear implant. As used herein, a totally implantable cochlear implant refers to an implant that is capable of operating, at least for a period of time, without the need for any external device. It would be appreciated that embodiments of the present invention may also be implemented in a cochlear implant that includes one or more external components. It would be further appreciated that embodiments of the present invention may be implemented in any partially or fully implantable hearing prosthesis now known or later developed, including, but not limited to, acoustic hearing aids, auditory brain stimulators, middle ear mechanical stimulators, hybrid electro-acoustic prosthesis or other prosthesis that electrically, acoustically and/or mechanically stimulate components of the recipient's outer, middle or inner ear.

Figure 1A:
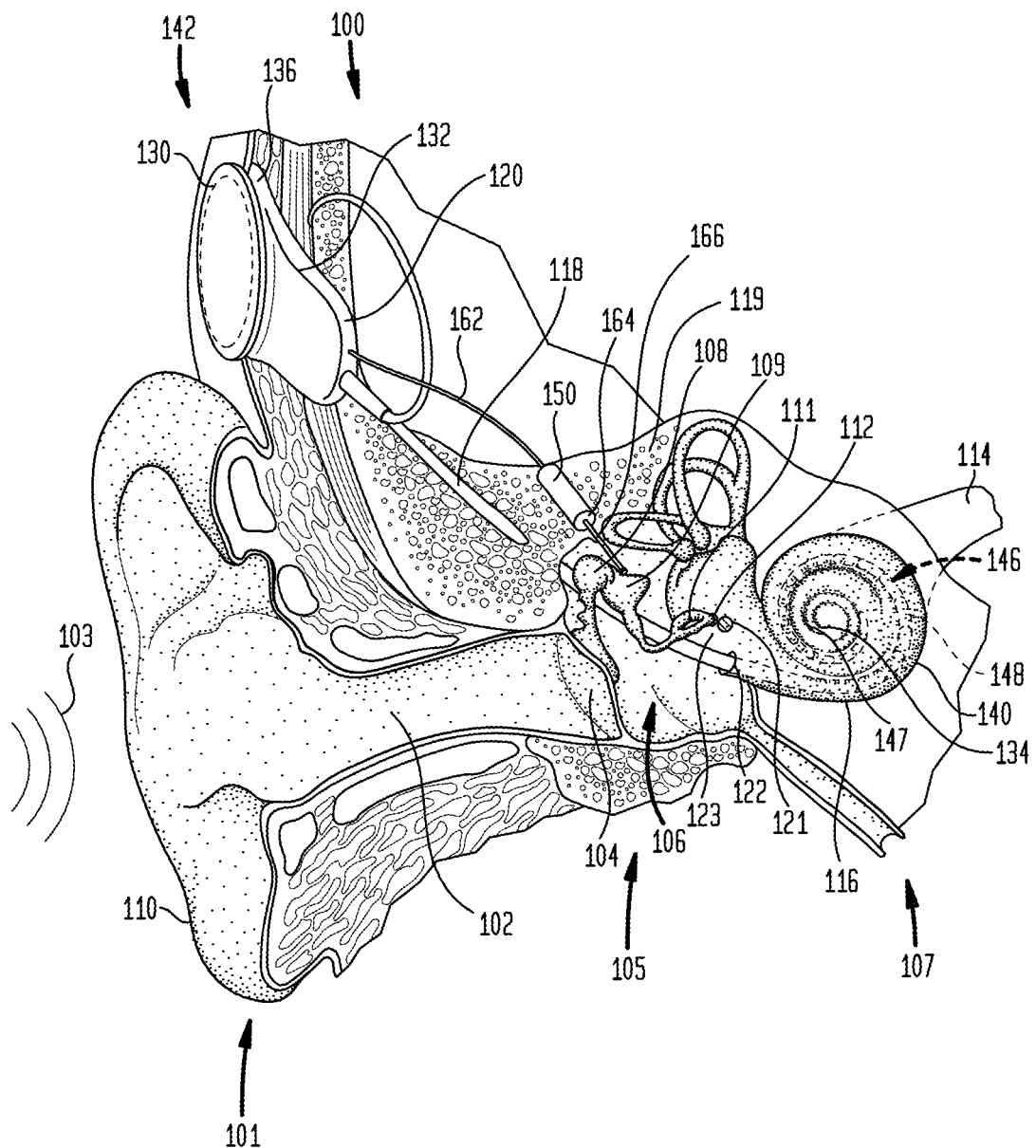
FIG. 1A is a schematic illustrating a hearing prosthesis implanted in a recipient, in accordance with certain embodiments presented herein.
Figure 1B:
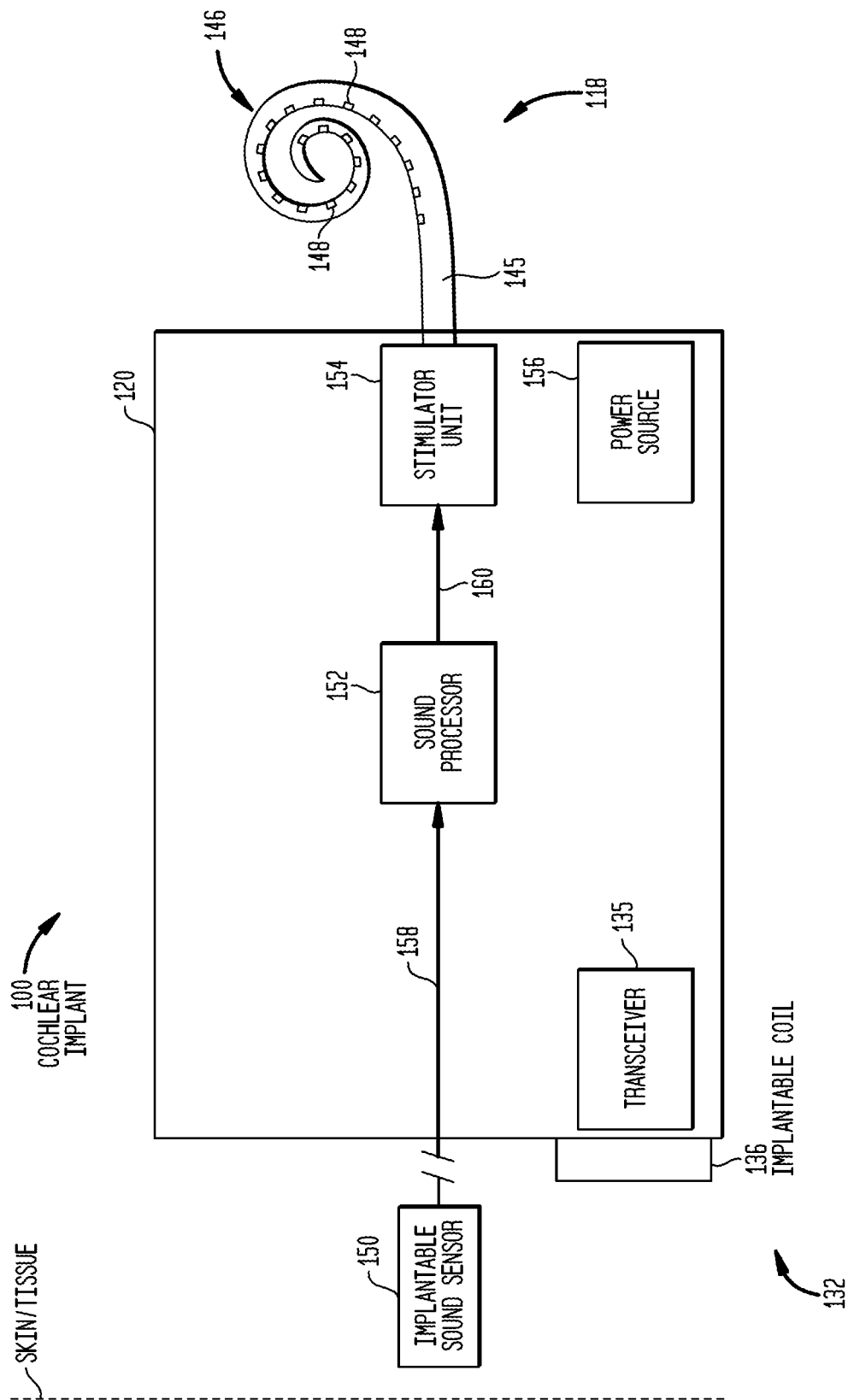
FIG. 1B is a schematic block diagram of the hearing prosthesis of FIG. 1A.

FIG. 1A is perspective view of a totally implantable cochlear implant, referred to as cochlear implant 100, implanted in a recipient. FIG. 1B is a block diagram of the cochlear implant 100. For ease of description, FIGS. 1A and 1B will be described together.

The recipient in which cochlear implant 100 is implanted has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises components which are temporarily or permanently implanted in the recipient (i.e., under the skin/tissue of the recipient). Cochlear implant 100 is shown in FIG. 1A with an external device 142 which, as described below, is configured to provide power to the cochlear implant.

In the illustrative arrangement of FIGS. 1A and 1B, the external device 142 may comprise a power source (not shown) disposed in an off-the ear (OTE) housing. As such, the external device 142 is sometimes referred to as an OTE unit or OTE component 142. The OTE component 142 also includes components of a transcutaneous energy transfer link, referred to as an external energy transfer assembly. The transcutaneous energy transfer link is used to transfer power (and in certain cases data) to cochlear implant 100. As would be appreciated, various types of energy transfer, such as infrared (IR), electromagnetic, capacitive and inductive transfer, may be used to transfer the power and/or data from OTE component 142 to cochlear implant 100. In the illustrative embodiments of FIG. 1A, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. OTE component 142 also includes a magnet (not shown) positioned within the turns of wire of external coil 130. It should be appreciated that the external device shown in FIG. 1A is merely illustrative, and other external devices, such as a behind-the ear (BTE) component may be used with embodiments of the present invention.

Cochlear implant 100 further comprises a main implantable component 120, an elongate electrode assembly 118, and an implantable sound sensor 150. The main implantable component 120 comprises an internal energy transfer assembly 132, a sound processor 152, stimulator unit 154, and a power source 156. The internal energy transfer assembly 132, which is a component of the transcutaneous energy transfer link, comprises a primary internal/implantable coil 136 and transceiver 135 configured to receive power (and possibly data) from OTE component 142. In the illustrative embodiment, the energy transfer link comprises an inductive RF link and implantable coil 136 is a wire antenna coil comprised of multiple turns of electrically insulated single-strand or multi-strand platinum or gold wire.

The sound sensor 150 is implanted in a cavity formed in mastoid bone 119 so as to extend, in this embodiment, into the middle ear cavity. Sound sensor 150 may be secured within the recipient via bracket or other mounting unit (not shown in FIG. 1A or 1B).

In operation, sound sensor 150 is configured to detect sound received in a recipient's ear through the use of vibrations or pressure variations that occur in or along the natural path that is followed by acoustic waves in the ear. More specifically, sound sensor 150 senses vibration of a structure of the recipient's middle ear 105, such as ossicles 106, or inner ear 107, such as vibration of fluid within one of the recipient's body cavities (e.g., inner ear canals, cochlear ducts, etc.). The vibration of the recipient's ear structure, referred to herein as "vibrating structure," is the result of receipt of acoustic waves that travel from the recipient's outer ear 101 to the middle ear 105 and inner ear 107. That is, the received acoustic waves impinge upon the vibrating structure of the middle or inner ear structures, creating vibration of the vibrating structure. In the embodiment illustrated in FIG. 1A, the sound sensor 150 detects sound based on vibration of the recipient's middle ear bones, and more specifically, based on vibration of incus 109 (i.e., incus 109 is the vibrating structure in FIG. 1A).

As described further below, the implantable sound sensor 150 comprises a non-uniform diaphragm 164 (FIG. 1A) mechanically coupled to the incus 109 via a coupling member 166 (FIG. 1A). As such, the non-uniform diaphragm 164 vibrates in response to vibration of incus 109. The sound sensor 150 includes a vibration sensor (not shown in FIG. 1A or 1B) that is configured to detect vibration of the non-uniform diaphragm 164 and convert the detected vibrations into electrical signals, sometimes referred to herein as microphone signals, which are provided to the sound processor 152 in the main implantable component 120 (e.g., via a cable). In FIG. 1B, these microphone signals are represented by arrow 158. The sound processor 152 is configured convert the microphone signals 158 received from the implantable sound sensor 150 into data signals, represented in FIG. 1B by arrow 160. The stimulator unit 154 generates electrical stimulation signals based on the data signals 160. The electrical stimulation signals are delivered to the recipient via elongate electrode assembly 118.

More specifically, elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123, or through an apical turn 147 of cochlea 140.

Electrode assembly 118 comprises a carrier member 145 formed from a resiliently flexible material, and a longitudinally aligned and distally extending array 146 of electrodes 148, sometimes referred to as electrode array 146 herein, disposed along a length of the carrier member 145. Although electrode array 146 may be disposed on the carrier member 145, in most practical applications, the electrode array 146 is integrated into the carrier member 145. As such, electrode array 146 is referred to herein as being disposed in carrier member 145. As noted, a stimulator unit 154 generates stimulation signals which are applied by electrodes 148 to cochlea 140, thereby stimulating auditory nerve 114.

As noted, cochlear implant 100 comprises a totally implantable prosthesis that is capable of operating, at least for a period of time, without the need for OTE component 142. Therefore, cochlear implant 100 further comprises a rechargeable power source 156 that stores power received from OTE component 142. The power source 156 may comprise, for example, a rechargeable battery. During operation of cochlear implant 100, the power stored by the power source 156 is distributed to the various other implanted components as needed. Although FIG. 1B shows the power source 156 located in main implantable component 120, in other embodiments the power source 156 may be disposed in a separate implanted location.

Figure 2A:
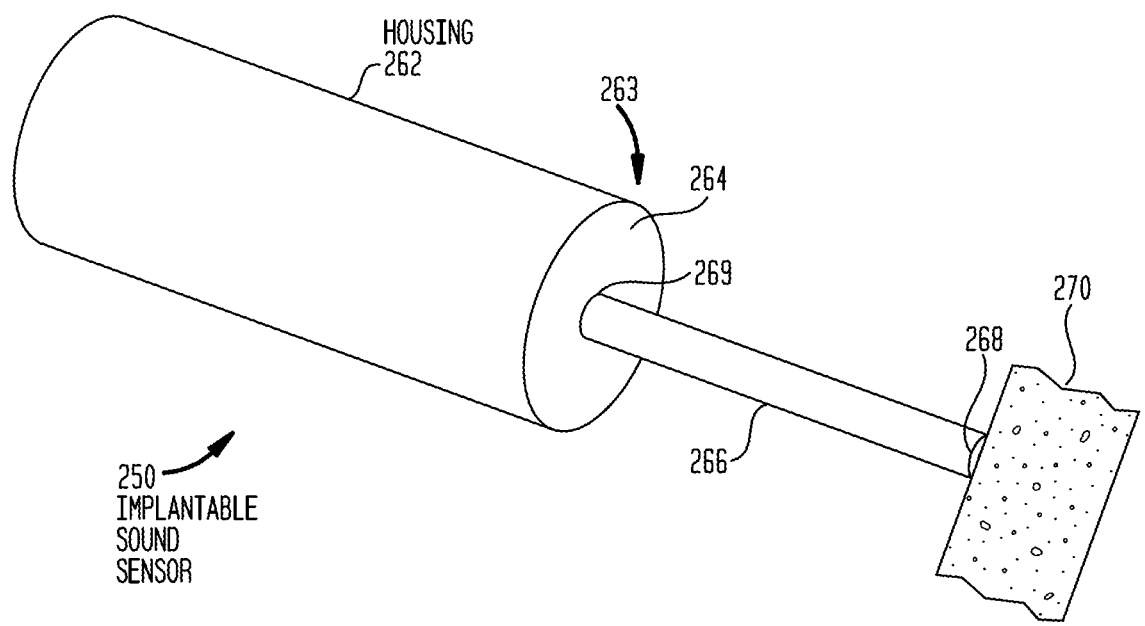
FIG. 2A is a schematic side view of an implantable sound sensor having a non-uniform diaphragm coupled to a vibrating structure of a recipient, in accordance with certain embodiments presented herein.
Figure 2B:
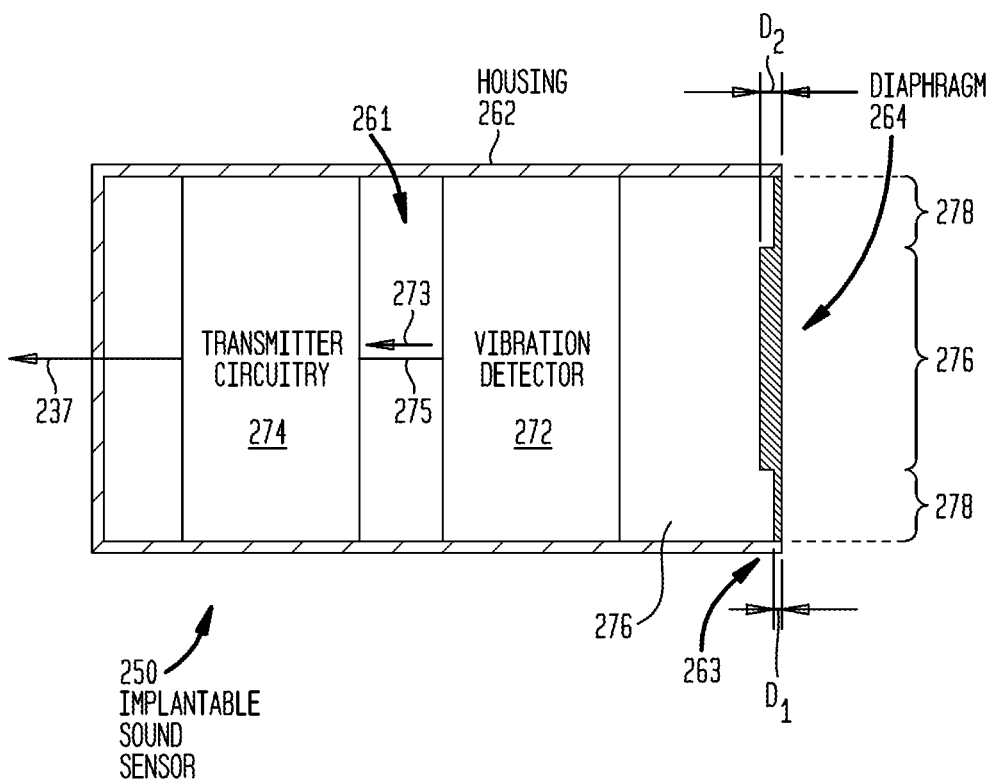
FIG. 2B is a schematic cross-sectional view of the implantable sound sensor of FIG. 2A.
Figure 2C:
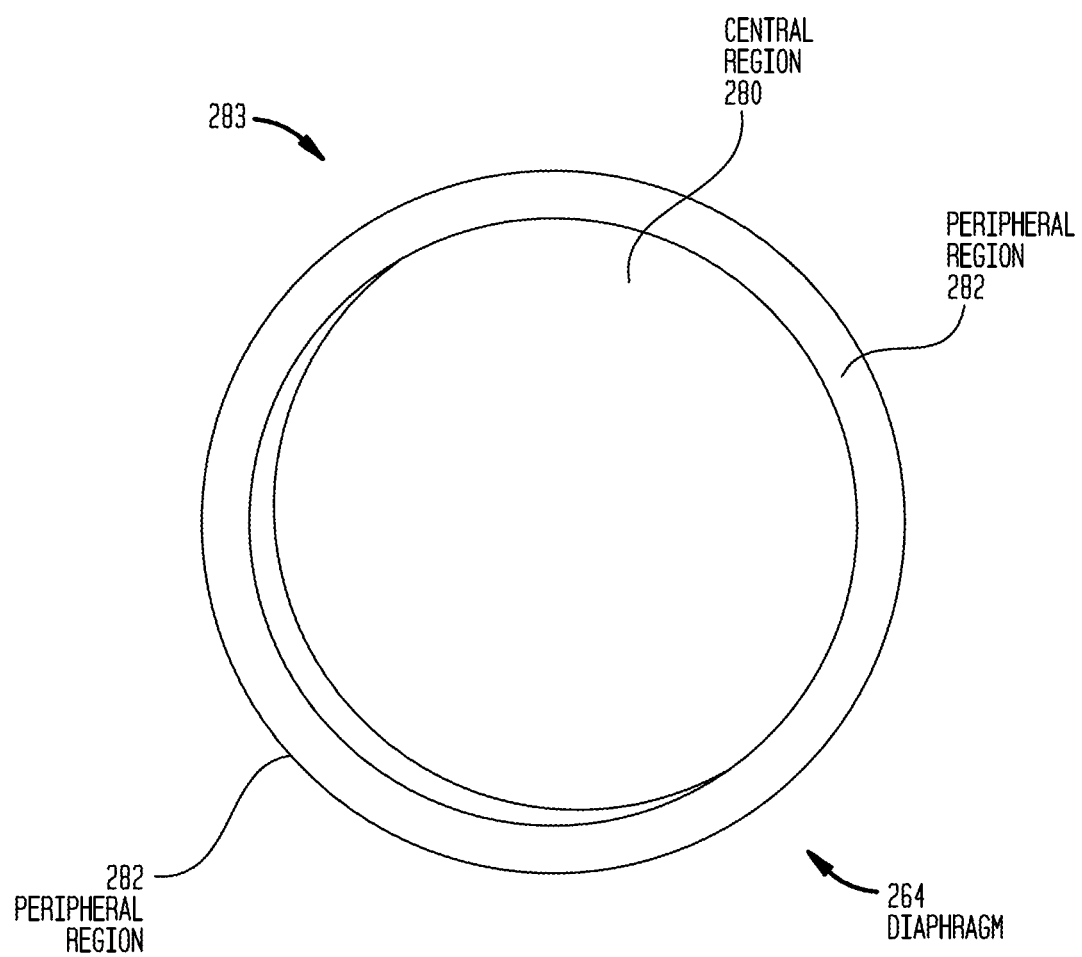
FIG. 2C is bottom-perspective view of the non-uniform diaphragm of the implantable sound sensor of FIG. 2A FIGS. 3A, 3B, and 3C are cross-sectional views illustrating operation of a conventional diaphragm.

An embodiment of implantable sound sensor 150 is described next below with reference to FIGS. 2A and 2B, referred to herein as implantable sound sensor 250 comprising a non-uniform diaphragm 264. FIG. 2A is a schematic perspective view of the implantable sound sensor 250, while FIG. 2B is a cross-sectional view of the implantable sound sensor 250. FIG. 2C is a bottom-perspective of the non-uniform diaphragm 264 separated from the rest of the implantable sound sensor 250. For ease of description, FIGS. 2A-2C will be described together.

The implantable sound sensor 250 includes a biocompatible housing 262 defining a cavity 261 with an opening at a first end 263 of the housing. The diaphragm 264 is disposed at the first end 263 of the housing 262. In particular, the diaphragm 264 is attached to the housing 262 so as to hermetically seal the opening at the first end 263 of the housing (i.e., prevent the ingress of bodily fluids into the housing 262). The diaphragm 264 may be welded to the housing 262, formed with (e.g., unitary with) the housing, etc.

In the example of FIGS. 2A and 2B, the housing 262 has a substantially tubular shape. The tubular shape may have a cylindrical or elliptical cross-sectional shape. Other shapes, such as prismatic with square, rectangular, or other polygonal cross-sectional shapes may also be used in alternative embodiments. However, a cylindrical shape may be advantageous for purposes of implantation and manufacture.

The implantable sound sensor 250 also comprises a coupling member 266 having a first end 268 and a second end 269. The first end 268 of the coupling member 266 is mechanically coupled to a vibrating structure 270 (e.g., ossicles) of a recipient's body, while the second end 269 of the coupling member 266 is secured to the non-uniform diaphragm 264.

The vibrating structure 270 of the recipient's body is a part of the recipient's body, such as part of the recipient's middle or inner ear, which is configured to vibrate as a result of the receipt of acoustic waves that travel from the recipient's outer ear to the middle ear and/or inner ear 107. That is, the received acoustic waves result in the vibration of the middle or inner ear structures, or travel through the middle ear cavity, creating vibration of the fluid within the cavities. The vibrating structure 270 may be, for example, any of the recipient's eardrum, ossicles (including any of the malleus, incus, or stapes), oval window, round window, horizontal canal, posterior canal, superior canal, etc. A physician, surgeon, or other trained medical professional typically makes the determination of which inner or middle ear structure to mechanically couple to the first end 268 of the coupling member 266.

The mechanical coupling between the first end 268 of the coupling member 266 and the vibrating structure 270 may be accomplished in a variety of ways. For example, in some embodiments, the first end 268 can be a surface-to-surface mechanical contact with a slight loading force to hold the first end 268 in place against the vibrating structure 270. In other embodiments, the first end 268 may be secured to the vibrating structure 270 with bone cement or another type of biocompatible adhesive.

As noted above, the second end 269 of the coupling member 266 is secured/attached to the non-uniform diaphragm 264. As such, the vibrations of the vibration structure 270 are relayed to the non-uniform diaphragm 264 via (through) the coupling member 266. As described further below, the non-uniform diaphragm 264 is flexible and configured to vibrate in response to vibration of the coupling member 266.

As noted, the diaphragm 264 is disposed at the first end 263 of the housing 262. Disposed in the housing 262 is a vibration sensor 272 and transmitter circuitry (transmitter) 274. The vibration sensor 272 may be any of an electret microphone, an electromechanical microphone, a piezoelectric microphone, a microelectro-mechanical systems (MEMS) microphone, an accelerometer, an optical interferometer, a pressure sensor, or any other type of vibration sensor now known or later developed. A gas (air) or liquid-filled vibration chamber 276 exists between the diaphragm 264 and the vibration sensor 272. For example, in embodiments where the vibration sensor 272 is an electret microphone, MEMS microphone, accelerometer, or optical interferometer, the vibration chamber 276 may be filled with gas such as helium or another gas. For embodiments where the vibration sensor 272 is a piezoelectric microphone or pressure sensor, the vibration chamber 276 may be filled with a liquid such as an oil, silicone gel, or other liquid. In operation, the vibration sensor 272 is configured to detect vibration/deflection of the diaphragm 264 and generate electrical signals 273 based at least in part on the detected vibrations.

In certain embodiments, electrical signals 273 generated by the vibration sensor 272 are provided to the transmitter circuitry 274 via a wire 275 or other similar electrical connection mechanism. The transmitter circuitry 274 may include one or more discrete circuit components, one or more integrated circuits, and/or a special-purpose processor configured to prepare or condition the electrical signals 273 (e.g., amplification, etc.) for transmission to a sound processor, such as sound processor 152 shown and described with respect to FIG. 1B. The transmitter circuitry 274 is configured to send the raw or conditioned/processed electrical signals, referred to herein as microphone signals, to the sound processor via a wired or wireless communications link (not shown in FIGS. 2A and 2B). The communications link, which is represented in FIG. 2B by arrow 237 may, in certain embodiments, also be used to provide operating power to the implantable sound sensor 250 in some embodiments.

As noted above, the non-uniform diaphragm 264 is flexible and configured to vibrate in response to vibration of the coupling member 266. Additionally, in the embodiments presented herein, the non-uniform diaphragm 264 is comprised of (formed as) multiple different sections/portions that have different thicknesses. More specifically, as shown in FIGS. 2B and 2C, the non-uniform diaphragm 264 comprises a first or central section/region 280 having a first thickness ($D_1$) and a second or peripheral section/region 282 having a second thickness ($D_2$) that is less than the thickness of the central region 280. As shown in FIG. 2C, the central region 280 has a general cylindrical shape (circular cross-sectional shape), and the peripheral region 282 comprises a ring-shape surrounding the central region 280 (i.e., extending around the outer edge of the central region 280). That is, the non-uniform diaphragm 264 has a greater thickness in the geometric center/middle of the diaphragm 264, and less thickness at the outer perimeter (periphery) of the diaphragm 264. The diaphragm 264 is referred to as "non-uniform diaphragm" due to the fact that thickness of the diaphragm 264 is greatest at geometric center of the diaphragm 264, and because the thickness is non-consistent throughout the diaphragm 264 is sometimes referred herein as a "centralized non-uniform diaphragm" or, more simply, as an "non-uniform diaphragm."

As shown in FIG. 2B, the non-uniform diaphragm 264 may be described as having a total area 283, where a portion of the total area 283 is formed by the central region 280 and a portion of the total area 283 is formed by the peripheral region 282. It is to be appreciate that the size of the central region 280 relative to the size of the total area 283 and the size of the peripheral region 282 may vary in different embodiments presented herein. In certain examples, the central region 280 may form at least approximately fifty (50) percent (%) of the total area 283 of the diaphragm 264. In further examples, the central region 280 may form at least approximately 50% of the total area 283 of the diaphragm 264, but less than approximately seventy-five (75) % of the total area 282 of the diaphragm 264.

In accordance with certain embodiments presented herein, the central region 280 and the peripheral region 282 are unitary/integrated and formed from the same material. For example, the central region 280 and the peripheral region 282 may each be made from titanium, a titanium alloy, or another biocompatible materials configured to hermetically seal end 262 of the housing 262 and to vibrate in response to movement of coupling member 266.

In certain embodiments in which the central region 280 and the peripheral region 282 are unitary, the non-uniform diaphragm 264 may be formed using a laser micro-machining process where material is removed to form the thinner regions/sections of the non-uniform diaphragm 264 (e.g., start with a cylinder-shaped piece of material and remove portions around the outer edge to form the thinner peripheral region). In other embodiments in which the central region 280 and the peripheral region 282 are unitary, the non-uniform diaphragm 264 may be formed using a surface deposition process where material is added to form the thicker central region (e.g., start with a planar/flat membrane and add/deposit material on the surface thereof to form the thicker central region).

In other embodiments, the central region 280 and the peripheral region 282 may be separate components that are attached to one another. For example, the peripheral region 282 could be formed as a planar membrane and the central region 280 could be attached to the surface thereof (e.g., via welding, using an adhesive, etc.).

As described further below, the increased thickness of the central region 280, relative to the thickness of the peripheral region 282, results in mechanics (mechanical operation) for the non-uniform diaphragm 264 that are significantly different than those of conventional diaphragms that have a substantially constant thickness, particularly when coupled to a vibrating structure of a recipient's body. This is illustrated with reference to FIGS. 3A-3C and FIGS. 4A-4C, where FIGS. 3A-3C are schematic cross-sectional diagrams illustrating operation of a conventional diaphragm of an implantable sound sensor, while FIGS. 4A-4C are simplified schematic diagrams illustration operation of a non-uniform diaphragm of an implantable sound sensor, in accordance with embodiments presented herein.

Figure 3A:
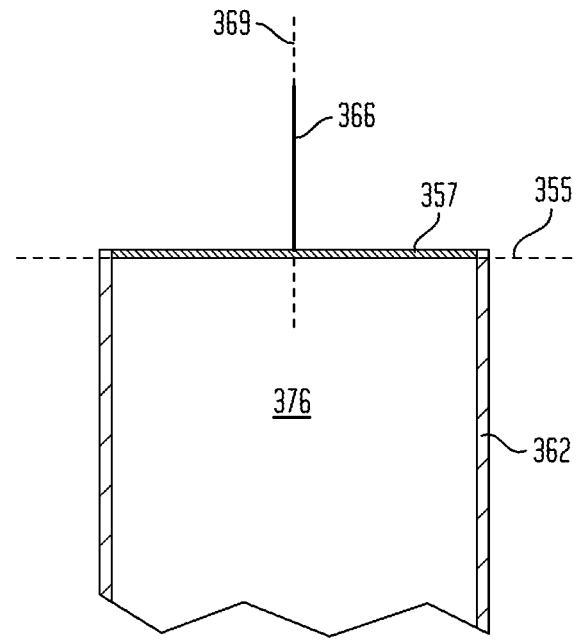
Figure 3B:
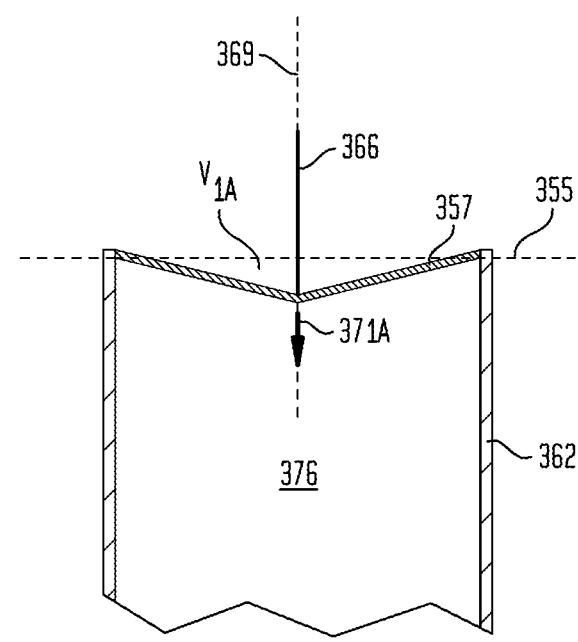
Figure 3C:
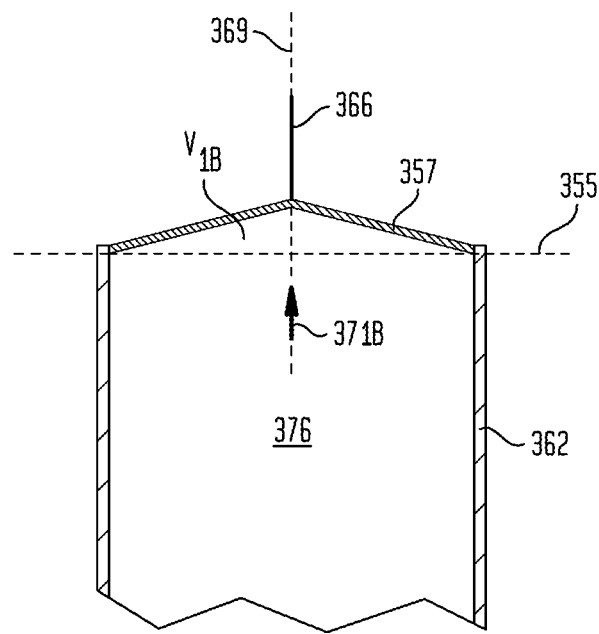
Figure 4A:
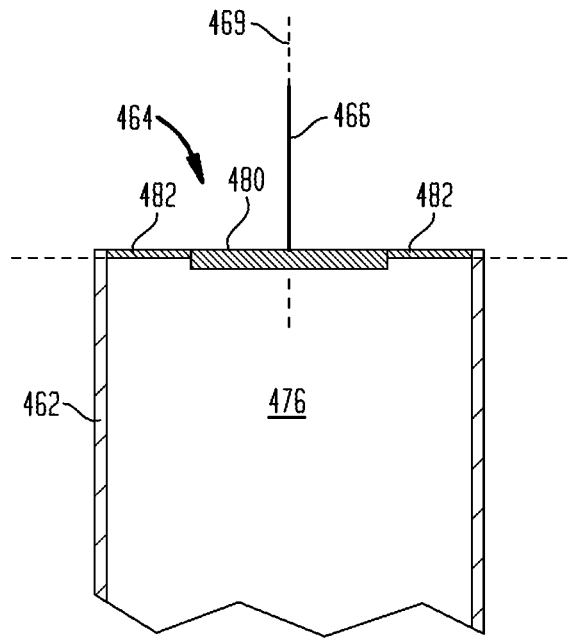
FIGS. 4A, 4B, and 4C are cross-sectional views illustrating operation of a non-uniform diaphragm, in accordance with certain embodiments presented herein.
Figure 4B:
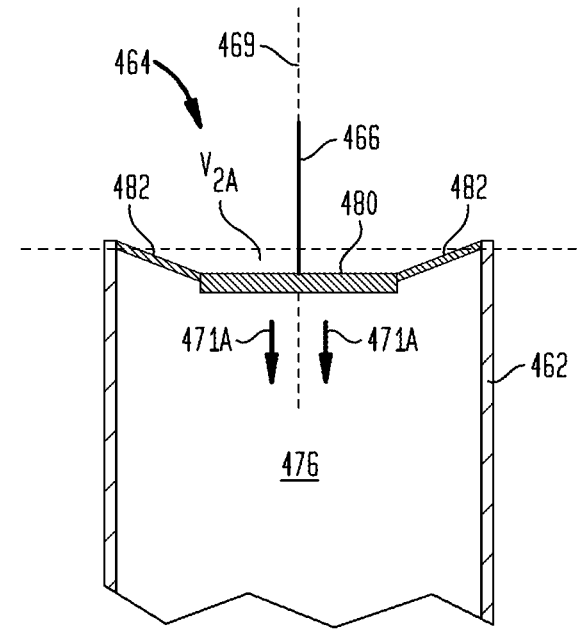
Figure 4C:
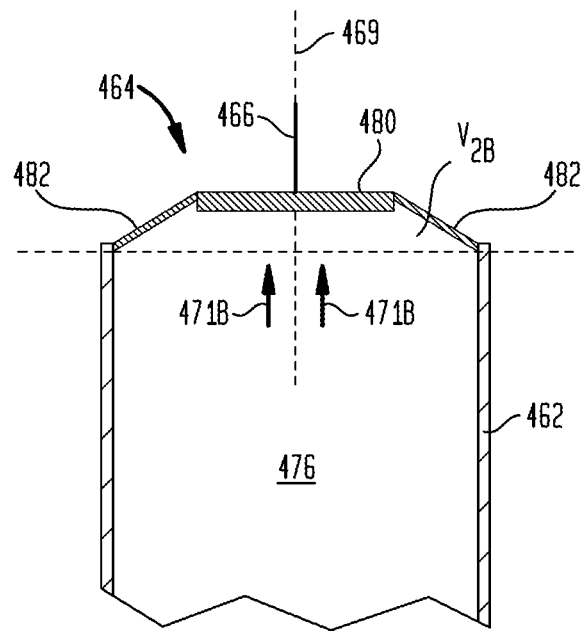

Referring first to FIG. 3A, shown is a simplified cross-sectional view of a conventional diaphragm 357 mechanically attached to a housing 362 and to a coupling member 366. The coupling member 366 mechanically couples the diaphragm 357 to a vibrating structure (not shown in FIGS. 3A-3C) of a recipient. The diaphragm 357 is shown in FIG. 3A at a resting or default position, there the diaphragm 357 is substantially in-line with a reference axis 355.

In operation, the vibrating structure vibrates in response to an acoustic signal (sound wave) received via the recipient's outer ear. This vibration of the vibrating structure imparts vibration to the coupling member 366 which, in turn, imparts vibration to the diaphragm 357 along a vibrational axis 369. The vibration of the diaphragm 357 is shown in FIGS. 3B and 3C by arrows 371A and 371B, respectively. That is, as shown by arrow 371A, the diaphragm 357 will deform/deflect into a vibration chamber 376 that exists between the diaphragm 357 and a vibration sensor (not shown in FIGS. 3A-3C) and, as shown by arrow 371B, the diaphragm 357 will deform/deflect away from the chamber 376 of the housing 362. This vibration of the diaphragm 357 causes movement/displacement of the contents (e.g., gas or liquid) of the vibration chamber 376.

Due to the mechanical attachment of the coupling member 366 to the diaphragm 357, and due to the uniform thickness of the diaphragm 357, the maximum displacement of the diaphragm 357 is localized to the relatively small area where the coupling member 366 is attached to the diaphragm 357. That is, as shown in FIGS. 3B and 3C, maximum displacement occurs only at the area of the diaphragm 357 that is localized to the vibrational axis 369 (i.e., only the area at which the diaphragm 357 is physically attached to the coupling member 366). The amount of displacement then decreases in a substantially uniform manner as a function of lateral distance from the vibrational axis 369. For ease of description, this type of conventional diaphragm displacement shown in FIGS. 3B and 3C is referred to herein as "localized" maximum displacement.

The result of the localized maximum displacement of diaphragm 357 is, as shown in FIG. 3B, a first displacement volume ($V_{1A}$) in the direction of 371A, and, as shown in FIG. 3C, a second displacement volume ($V_{1B}$) in the direction of 371B. The displacement volumes $V_{1A}$ and $V_{1B}$ refer the volume of the contents of chamber 376 that is displaced at the point of maximum displacement of the diaphragm 357, in directions 371A and 371B, respectively, for a given acoustic signal (sound wave) received at (i.e., impinging on) the vibrating structure. These displacement volumes $V_{1A}$ and $V_{1B}$ are what is detected by the vibration sensor within the housing 362.

Referring next to FIG. 4A, shown is a simplified cross-sectional view of a non-uniform diaphragm 464 in accordance with embodiments presented herein. In the examples of FIGS. 4A-4C, the non-uniform diaphragm 464 has the same general arrangement as non-uniform diaphragm 264 of FIGS. 2A-2C. In particular, non-uniform diaphragm 464 is comprised of a central region 480 having a first thickness ($D_1$) and a peripheral region 482 having a second thickness ($D_2$) that is less than the first thickness of central region 480. The central region 480 has a general cylindrical shape, and the peripheral region 482 comprises a ring-shape surrounding the central region 480 (i.e., extending around the outer edge of the central region 480). That is, diaphragm 464 has a greater thickness in the geometric center/middle of the diaphragm 464, and less thickness at the outer perimeter (periphery) of the diaphragm 464.

As shown, the non-uniform diaphragm 464 is mechanically attached to a housing 462 and to a coupling member 466. The coupling member 466 mechanically couples the diaphragm 464 to a vibrating structure (not shown in FIGS. 4A-4C) of a recipient. The diaphragm 464 is shown in FIG. 4A at a resting or default position, there the diaphragm 464 is substantially in-line with a reference axis 455.

In operation, the vibrating structure vibrates in response to an acoustic signal (sound wave) received via the recipient's outer ear. This vibration of the vibrating structure imparts vibration to the coupling member 466 which, in turn, imparts vibration to the non-uniform diaphragm 464 along a vibrational axis 469. The vibration of the non-uniform diaphragm 464 is shown in FIGS. 4B and 4C by arrows 471A and 471B, respectively. That is, as shown by arrow 471A, the non-uniform diaphragm 464 will deform/deflect into a vibration chamber 476 that exists between the non-uniform diaphragm 464 and a vibration sensor (not shown in FIGS. 4A-4C) and, as shown by arrow 471B, the non-uniform diaphragm 464 will deform/deflect away from the vibration chamber 476 of the housing 462. This vibration of the non-uniform diaphragm 464 causes movement/displacement of the contents (e.g., gas or liquid) of vibration chamber 476.

As noted above with reference to FIGS. 3A-3C, with conventional diaphragms having a uniform thickness, mechanically coupled vibration causes maximum displacement of the conventional diaphragm only at the area of the diaphragm that is localized to the vibrational axis. However, as shown in FIGS. 4B and 4C, the mechanical properties of non-uniform diaphragms presented herein, such as non-uniform diaphragm 464, result in a significantly different (i.e., increased) area of maximum displacement. More particularly, due to the mechanical attachment of the coupling member 466 to the diaphragm 464, and due to the non-uniform thickness of the diaphragm 464, the maximum displacement of the diaphragm 464 occurs generally across the substantial entirety of the central region 480. The amount of displacement then beings to decrease at the junction of the central region 480 and the peripheral region 482 (i.e., in the area of the diaphragm that transitions from thicker to thinner). The displacement then decreases across peripheral region 482, in a substantially uniform manner as a function of lateral distance from the vibrational axis 469. Stated differently, the greater thickness of the central region 480 relative to the peripheral region 482 causes the substantial entirety of the central region 480 (i.e., substantially all of the thicker section) to move in response to the vibration from the coupling element 466, while the peripheral region 482 deforms. For ease of description, this type of diaphragm displacement shown in FIGS. 4B and 4C is referred to herein as "distributed" maximum displacement.

As noted above, the size of a central region of a non-uniform diaphragm may vary in different embodiments presented herein. For example, the central region 480 of non-uniform diaphragm 464 may form at least approximately 50% of the total area of the diaphragm 464. Therefore, in such embodiments, at least approximately 50% of the diaphragm 464 reaches maximum displacement in response to a given acoustic signal.

The result of the distributed maximum displacement of diaphragm 464 is, as shown in FIG. 4B, a first displacement volume ($V_{2A}$) in the direction of 471A, and, as shown in FIG. 4C, a second displacement volume ($V_{2B}$) in the direction of 471B. The displacement volumes $V_{2A}$ and $V_{2B}$ refer the volume of the contents of chamber 476 that is displaced at the point of maximum displacement of the diaphragm 464, in directions 471A and 471B, respectively, for a given acoustic signal received at the vibrating structure. These displacement volumes $V_{2A}$ and $V_{2B}$ are what is detected by the vibration sensor within the housing 462.

In general, if diaphragms 357 and 464 have the same outer dimension (e.g., diameter), coupled to the same vibrating structure by the same coupling member, the same acoustic signal will cause the diaphragm 464 to displace more content of the corresponding vibration chamber. That is, in this scenario (i.e., same acoustic signal, same vibrating structure, and same coupling), $V_{2A}$ is greater than $V_{1A}$ and $V_{2B}$ is greater than $V_{1B}$. The increased displacement volumes generated by non-uniform diaphragm 464, relative to the conventional diaphragms, means that non-uniform diaphragm 464, and the associated implantable sound sensor, become more sensitive to acoustic signals impinging upon the vibrating structure (i.e., more contents of the chamber is moved for the same acoustic signal in the embodiments presented).

As detailed above, in accordance with embodiments presented herein, the thickness of certain portions of the non-uniform diaphragms are increased in order to increase the overall sensitivity of the implantable sound sensor. That is, by changing the thickness, and thus stiffness, in the middle of the diaphragm, the techniques presented herein increase the sensitivity while keeping the same overall diameter when used with a mechanical coupling to vibrating structure of a recipient's anatomy (i.e., the microphone becomes more sensitive for the same form factor). Generally speaking, it is counter intuitive that a thicker diaphragm would provide increased sensitivity and provide better sound performance, as is the case with the non-uniform diaphragms presented herein. Instead, conventional thinking is that microphone sensitivity can be increased by increasing the diameter (i.e., total area) of the diaphragm and/or by reducing the thickness of the diaphragm (i.e., traditionally, the goal has been to make diaphragms as thin as possible so that they are most responsive).

FIGS. 2A and 2B, as well as FIGS. 4A-4C have been described with reference to one specific arrangement for a non-uniform diaphragm. However, it is to be appreciated that non-uniform diaphragms in accordance with embodiments presented herein may have a number of other physical arrangements that provide the non-uniform diaphragm with similar mechanics to that described with reference to FIGS. 4A-4C. Examples of such other suitable arrangements are shown in FIGS. 5-21. In each of FIGS. 5-21, the corresponding non-uniform diaphragms is comprised of a central region having a first thickness ($D_1$) and a peripheral region having a second thickness that is less than the first thickness of central region so as to operate in a similar manner as described above with reference to FIGS. 4A-4C.

Figure 5:
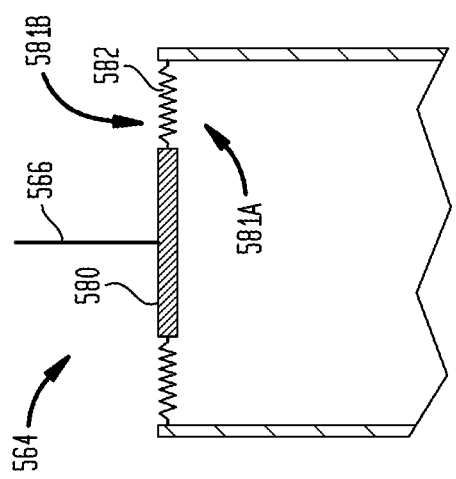
FIG. 5 is a cross-sectional view of a non-uniform diaphragm, in accordance with certain embodiments presented herein.

Referring first to FIG. 5, shown is a non-uniform diaphragm 564 in accordance with embodiments presented herein coupled to a coupling member 566. In the example of FIG. 5, the non-uniform diaphragm 564 is comprised of a central region 580 and a peripheral region 582. The central region 580 has a general cylindrical shape, while the peripheral region 582 comprises a ring-shape surrounding the central region 580 (i.e., extending around the outer edge of the central region 580). Although the peripheral region 582 has a general ring shape, it also has an undulating or ridged cross-sectional shape (i.e., has undulating or ridged inner and outer surfaces 581A and 581B, respectively). That is, in contrast of FIGS. 2B and 4A-4C where the peripheral region regions are generally planar members, the peripheral region 582 is an undulating member.

Figure 6:
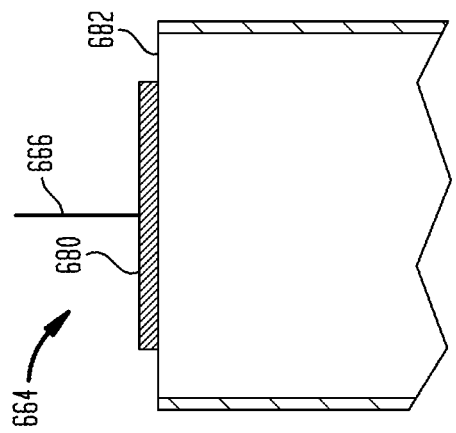
FIG. 6 is a cross-sectional view of a non-uniform diaphragm, in accordance with certain embodiments presented herein.

Referring next to FIG. 6, shown is a non-uniform diaphragm 664 in accordance with embodiments presented herein coupled to a coupling member 666. In the example of FIG. 6, the non-uniform diaphragm 664 is comprised of a central region 680 and a peripheral region 682. The central region 680 has a general cylindrical shape, while the peripheral region 682 comprises a ring-shape surrounding the central region 680 (i.e., extending around the outer edge of the central region 680).

In the examples of FIGS. 2B and 4A-4C, the corresponding cylindrical central regions were positioned at the inner surface of the diaphragms (i.e., the central regions extended into the vibration chamber of the implantable sound sensor). In the example of FIG. 6, the central region 680 is positioned at the outer surface of the diaphragm 664 (i.e., the central region 680 extends away from the vibration chamber of the implantable sound sensor).

Figure 7:
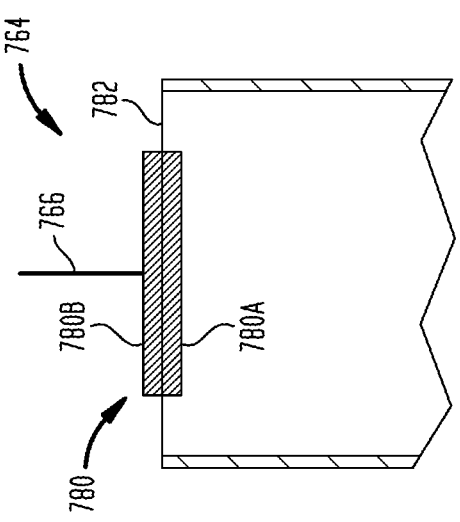
FIG. 7 is a cross-sectional view of a non-uniform diaphragm, in accordance with certain embodiments presented herein.

Referring next to FIG. 7, shown is a non-uniform diaphragm 764 in accordance with embodiments presented herein coupled to a coupling member 766. In the example of FIG. 7, the non-uniform diaphragm 764 is comprised of a central region 780 and a peripheral region 782. The central region 780 has a general cylindrical shape, while the peripheral region 782 comprises a ring-shape surrounding the central region 780 (i.e., extending around the outer edge of the central region 780).

In the examples of FIGS. 2B and 4A-4C, the corresponding cylindrical central regions were positioned at the inner surface of the diaphragms (i.e., the central regions extended into the vibration chamber of the implantable sound sensor). In the example of FIG. 7, the central region 780 is positioned at both the outer surface of the diaphragm 764, as well as the inner surface of the diaphragm 764. Stated differently, the central region 780 has a first portion 780A that extends into the vibration chamber of the implantable sound sensor, and a second portion 780B that extends away from the vibration chamber of the implantable sound sensor).

Figure 8:
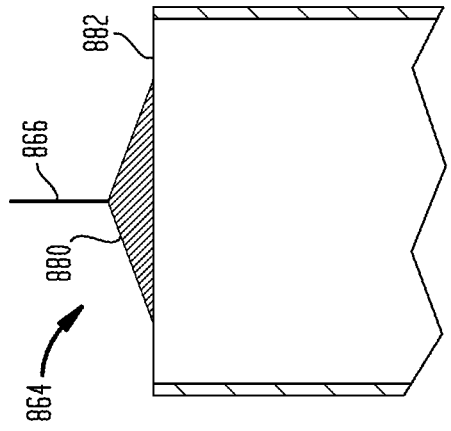
FIG. 8 is a cross-sectional view of a non-uniform diaphragm, in accordance with certain embodiments presented herein.

Referring next to FIG. 8, shown is a non-uniform diaphragm 864 in accordance with embodiments presented herein coupled to a coupling member 866. In the example of FIG. 8, the non-uniform diaphragm 864 is comprised of a central region 880 and a peripheral region 882. The central region 880 has a general conical shape, while the peripheral region 882 comprises a ring-shape surrounding the central region 880 (i.e., extending around the outer edge of the central region 880).

Figure 9:
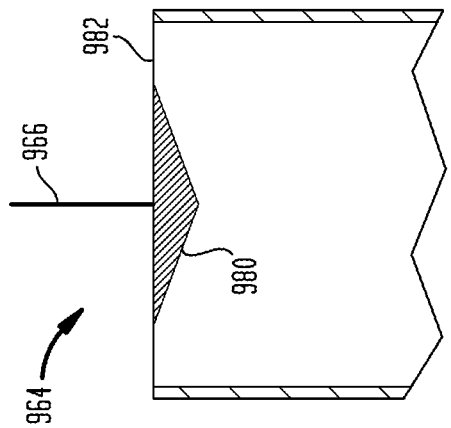
FIG. 9 is a cross-sectional view of a non-uniform diaphragm, in accordance with certain embodiments presented herein.

Referring next to FIG. 9, shown is a non-uniform diaphragm 964 in accordance with embodiments presented herein coupled to a coupling member 966. In the example of FIG. 9, the non-uniform diaphragm 964 is comprised of a central region 980 and a peripheral region 982. The central region 980 has a general conical shape, while the peripheral region 982 comprises a ring-shape surrounding the central region 980 (i.e., extending around the outer edge of the central region 980).

In the example of FIG. 8, the conical central region 880 is positioned at the outer surface of the diaphragm 864 (i.e., the central region 880 extends away from the vibration chamber of the implantable sound sensor). In the example of FIG. 9, the central region 980 is positioned at the inner surface of the diaphragm 964 (i.e., the central region 680 extends into the vibration chamber of the implantable sound sensor).

Figure 10:
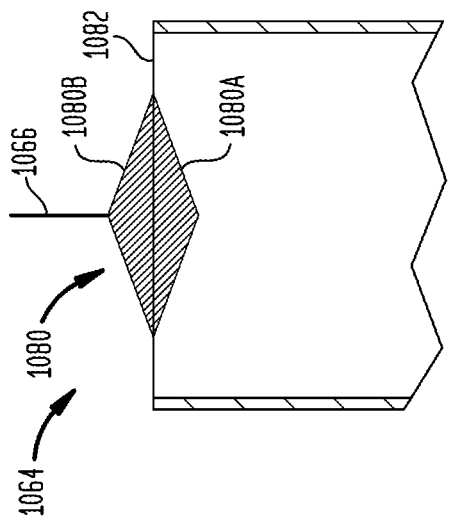
FIG. 10 is a cross-sectional view of a non-uniform diaphragm, in accordance with certain embodiments presented herein.

Referring next to FIG. 10, shown is a non-uniform diaphragm 1064 in accordance with embodiments presented herein coupled to a coupling member 1066. In the example of FIG. 10, the non-uniform diaphragm 1064 is comprised of a central region 1080 and a peripheral region 1082. The peripheral region 1082 comprises a ring-shape surrounding the central region 1080 (i.e., extending around the outer edge of the central region 1080). In the example of FIG. 10, the central region 1080 is positioned at both the outer surface of the diaphragm 1064, as well as the inner surface of the diaphragm 1064. Stated differently, the central region 1080 has a first conical portion 1080A that extends into the vibration chamber of the implantable sound sensor, and a second conical portion 1080B that extends away from the vibration chamber of the implantable sound sensor).

Figure 11:
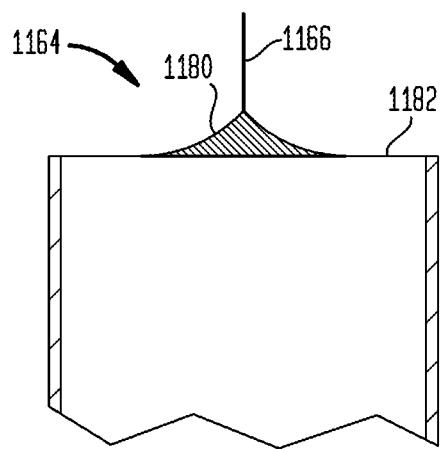
FIG. 11 is a cross-sectional view of a non-uniform diaphragm, in accordance with certain embodiments presented herein.

Referring next to FIG. 11, shown is a non-uniform diaphragm 1164 in accordance with embodiments presented herein coupled to a coupling member 1166. In the example of FIG. 11, the non-uniform diaphragm 1164 is comprised of a central region 1180 and a peripheral region 1182. The central region 1180 has an elongated conical shape, where the surfaces of the cone is defined by a non-liner curvature. The peripheral region 1182 comprises a ring-shape surrounding the central region 1180 (i.e., extending around the outer edge of the central region 1180).

Figure 12:
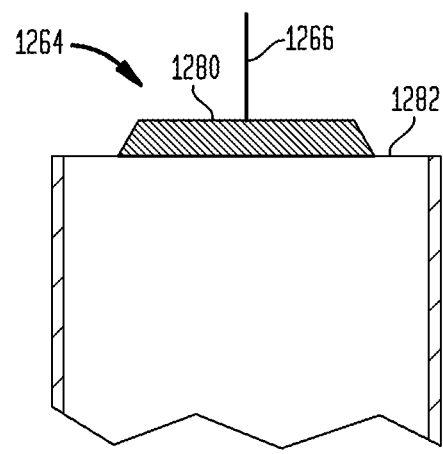
FIG. 12 is a cross-sectional view of a non-uniform diaphragm, in accordance with certain embodiments presented herein.

Referring next to FIG. 12, shown is a non-uniform diaphragm 1264 in accordance with embodiments presented herein coupled to a coupling member 1266. In the example of FIG. 12, the non-uniform diaphragm 1264 is comprised of a central region 1280 and a peripheral region 1282. The central region 1280 has a general flattened-conical shape, while the peripheral region 1282 comprises a ring-shape surrounding the central region 1280 (i.e., extending around the outer edge of the central region 1280).

Figure 13:
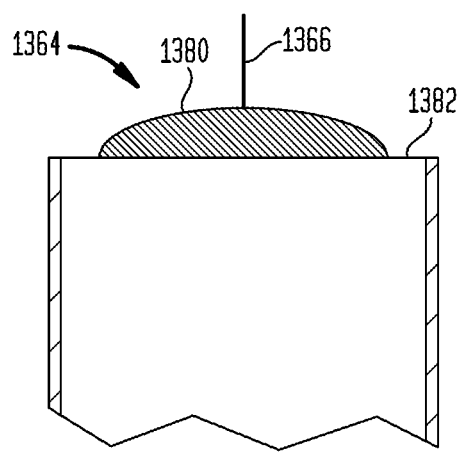
FIG. 13 is a cross-sectional view of a non-uniform diaphragm, in accordance with certain embodiments presented herein.
Figure 14:
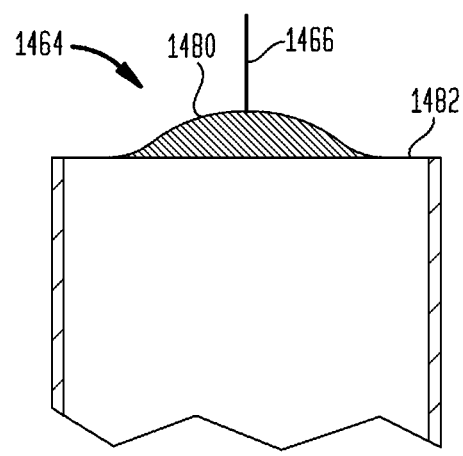
FIG. 14 is a cross-sectional view of a non-uniform diaphragm, in accordance with certain embodiments presented herein.

Referring next to FIG. 13, shown is a non-uniform diaphragm 1364 in accordance with embodiments presented herein coupled to a coupling member 1366. In the example of FIG. 13, the non-uniform diaphragm 1364 is comprised of a central region 1380 and a peripheral region 1382. The central region 1380 has a general tetrahedron or hemispherical shape, while the peripheral region 1382 comprises a ring-shape surrounding the central region 1380 (i.e., extending around the outer edge of the central region 1380). Referring next to FIG. 14, shown is a non-uniform diaphragm 1464 in accordance with embodiments presented herein coupled to a coupling member 1466. In the example of FIG. 14, the non-uniform diaphragm 1464 is comprised of a central region 1480 and a peripheral region 1482. The central region 1480 has a general paraboloid or parabolic shape, while the peripheral region 1482 comprises a ring-shape surrounding the central region 1480 (i.e., extending around the outer edge of the central region 1480).

Figure 15:
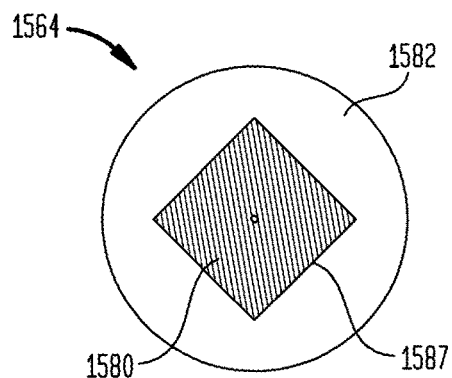
FIG. 15 is a cross-sectional view of a non-uniform diaphragm, in accordance with certain embodiments presented herein.

In general, FIGS. 5-14 illustrate non-uniform diaphragms having central regions each defined by a substantially-circular bases, where the peripheral region has a ring-shape surrounding the circular base of the central region. It is to be appreciated that the use of central regions having substantially-circular bases is illustrative and that other shapes are possible. For example, FIG. 15 is a top-view of a non-uniform diaphragm 1564 in accordance with embodiments presented herein having a central region 1580 and a peripheral region 1582. In this embodiment, the central region 1580 is defined by a substantially-square base 1587.

Figure 16:
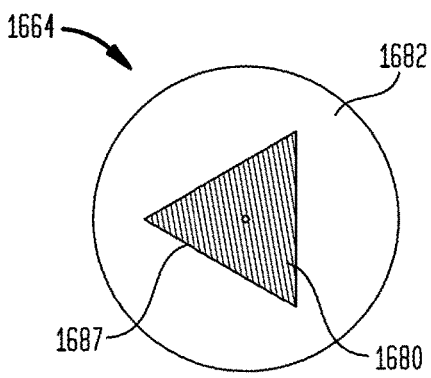
FIG. 16 is a cross-sectional view of a non-uniform diaphragm, in accordance with certain embodiments presented herein.

As another example, FIG. 16 is a top-view of a non-uniform diaphragm 1664 in accordance with embodiments presented herein having a central region 1680 and a peripheral region 1682. In this embodiment, the central region 1680 is defined by a substantially-triangular base 1687.

Figure 17:
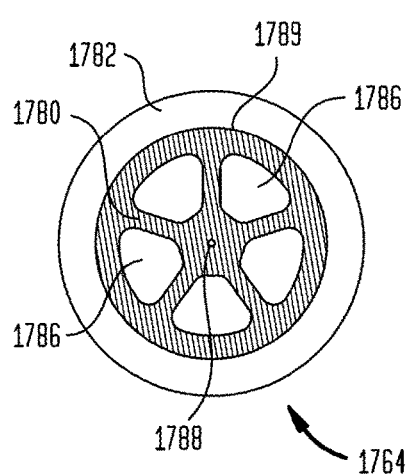
FIG. 17 is a cross-sectional view of a non-uniform diaphragm, in accordance with certain embodiments presented herein.
Figure 18:
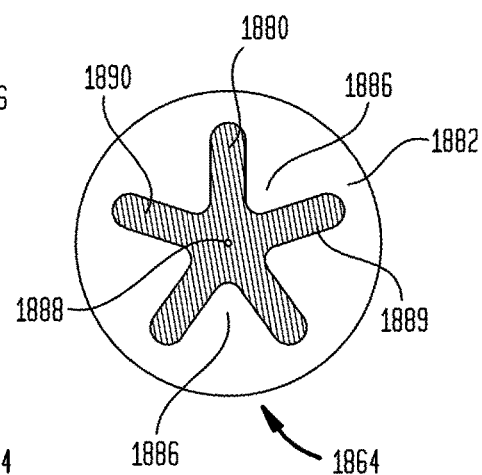
FIG. 18 is a cross-sectional view of a non-uniform diaphragm, in accordance with certain embodiments presented herein.
Figure 19:
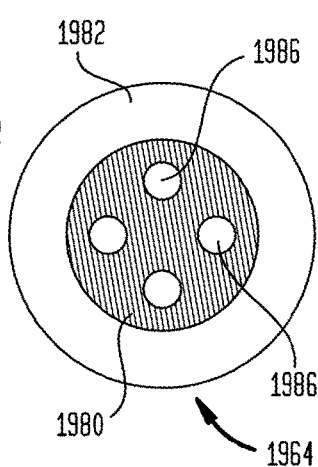
FIG. 19 is a cross-sectional view of a non-uniform diaphragm, in accordance with certain embodiments presented herein.

It is to be appreciated that, in certain embodiments presented herein, a central region of a non-uniform diaphragm may include one or more holes or cut-outs that may, for example, reduce weight of the central region relative to substantially solid central regions. FIGS. 17-19 are top views of non-uniform diaphragms that include cut-outs in the central regions thereof.

More specifically, first to FIG. 17, shown is a non-uniform diaphragm 1764 comprising a central region 1780 and a peripheral region 1782. In this example, the central region 1780 comprises a plurality of elongate cut-outs 1786 extending outward from a center 1788 of the central region 1780. In this example, the cut-outs 1786 terminate prior to outer edge 1789 of the central region 1780.

Referring next to FIG. 18, shown is a non-uniform diaphragm 1864 comprising a central region 1880 and a peripheral region 1882. In this example, the central region 1880 comprises a plurality of elongate cut-outs 1886 extending outward from a center 1888 of the central region 1880. In this example, the cut-outs 1886 extend to the outer edge 1889 of the central region 1880. Stated differently, the central region 1880 comprises a plurality of arms 1890 extending from the center 1888 thereof.

Referring next to FIG. 19, shown is a non-uniform diaphragm 1964 comprising a central region 1980 and a peripheral region 1982. In this example, the central region 1980 comprises a plurality of cylindrical channels 1986 extending longitudinally through the central region 1980.

As described above, FIG. 5, illustrates a non-uniform diaphragm 564 in accordance with embodiments presented herein that comprises a peripheral region 582 having an undulating or ridged cross-sectional shape (i.e., has undulating or ridged inner and outer surfaces 581A and 581B, respectively). That is, FIG. 5 illustrates an embodiment in which the peripheral region 582 is an undulating member.

Figure 20:
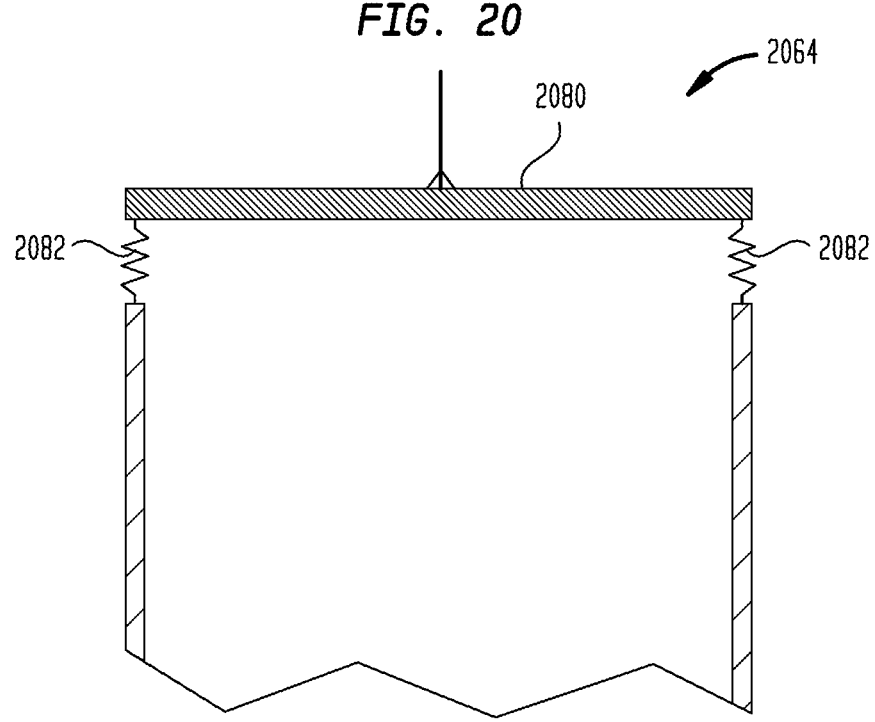
FIG. 20 is a cross-sectional view of a non-uniform diaphragm, in accordance with certain embodiments presented herein.

In FIG. 5, the undulating peripheral region 582 is substantially co-planar with the central region 580. It is to be appreciate that this co-planar arrangement of the undulating peripheral region 582 and the central region 580 is illustrative and that other arrangements may be used in embodiments presented herein. For example, FIG. 20 illustrates an embodiment of a non-uniform diaphragm 2064 in accordance with embodiments presented herein that comprises a central region 2080 and a peripheral region 2082 having an undulating or ridged cross-sectional shape. However, in this example, the peripheral region 2082 is substantially orthogonal to central region 2080 (i.e., the central region 2080 and peripheral region 2082 are not co-planar).

Figure 21:
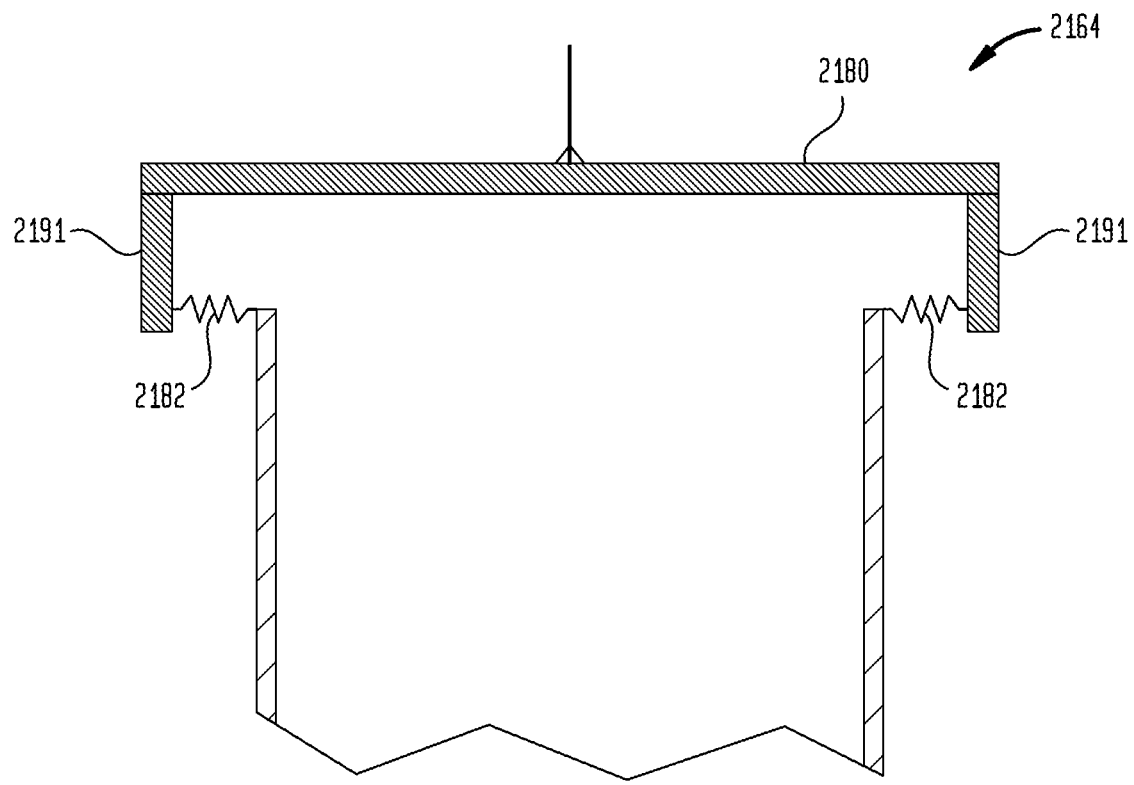
FIG. 21 is a cross-sectional view of a non-uniform diaphragm, in accordance with certain embodiments presented herein.

FIG. 21 illustrates another embodiment of a non-uniform diaphragm 2264 in accordance with embodiments presented herein that comprises a central region 2280 and a peripheral region 2082 having an undulating or ridged cross-sectional shape. However, in this example, the peripheral region 2282 is substantially parallel to a central region 2180 (i.e., the central region 2180 and peripheral region 2182 are positioned in substantially parallel planes). As shown in FIG. 21, the peripheral region 2182 is mechanically attached to the central region 2180 via a spacing element 2191. In certain embodiments, central region 2180, peripheral region 2182, and spacing element 2191 may be a unitary structure formed from the same material. In other embodiments, one or more of central region 2180, peripheral region 2182, and spacing element 2191 may be a discrete component that is joined to one or more of the other elements (e.g., via welding).

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A device comprising:
    a biocompatible housing defining a cavity and having an opening at a first end of the biocompatible housing;
    a non-uniform diaphragm attached to the biocompatible housing so as to hermetically seal the opening, the non-uniform diaphragm having at least a first section and a second section, wherein the second section is disposed around the first section and couples the first section to the biocompatible housing, and wherein the first section has a thickness that is greater than a thickness of the second section;
    a vibration sensor disposed in the biocompatible housing and configured to detect vibration of the non-uniform diaphragm and generate signals representative of the vibration; and
    a vibration chamber disposed in the biocompatible housing between the non-uniform diaphragm and the vibration sensor, wherein the first section is positioned at an outer surface of the non-uniform diaphragm such that the first section extends from the outer surface away from the vibration chamber.

2. The device of claim 1, wherein the first section of the non-uniform diaphragm comprises a central region disposed at a center of the non-uniform diaphragm, and wherein the second section of the non-uniform diaphragm comprises a peripheral region disposed around the central region and coupling the central region to the biocompatible housing.

3. The device of claim 2, wherein the peripheral region is substantially co-planar with the central region.

4. The device of claim 2, wherein the peripheral region comprises a ring-shape disposed around an outer edge of the central region.

5. The device of claim 1, further comprising:
    a coupling member configured to mechanically couple the first section of the non-uniform diaphragm to a vibrating structure of a middle ear or inner ear of a recipient such that the non-uniform diaphragm vibrates in response to vibration of the vibrating structure.

6. A device comprising:
    a biocompatible housing defining a cavity and an opening at one end;
    a diaphragm positioned at the opening defined in the biocompatible housing, the diaphragm having a first thickness at a central region of the diaphragm that is greater than a second thickness of a peripheral region of the diaphragm coupling the central region to the biocompatible housing, wherein the central region has a cylindrical shape, and wherein the peripheral region has a ring-shape and surrounding the central region;
    a vibration sensor disposed in the biocompatible housing and configured to detect vibration of the diaphragm and generate signals representative of the vibration;
    a vibration chamber disposed in the biocompatible housing between the diaphragm and the vibration sensor; and
    a coupling member configured to mechanically couple the central region of the diaphragm to a vibrating structure of a middle ear or an inner ear of a recipient.

7. The device of claim 6, wherein the central region is positioned at an inner surface of the diaphragm and at least partially extends into the vibration chamber.

8. The device of claim 6, wherein the central region includes at least a first portion positioned at an outer surface of the diaphragm, wherein the first portion extends away from the vibration chamber.

9. The device of claim 8, wherein the central region further includes a second portion positioned at an inner surface of the diaphragm, wherein the second portion extends into the vibration chamber.

10. The device of claim 6, wherein the peripheral region is substantially co-planar with the central region.

11. A device comprising:
    a biocompatible housing defining a cavity and having an opening at a first end of the biocompatible housing;
    a non-uniform diaphragm attached to the biocompatible housing so as to hermetically seal the opening, the non-uniform diaphragm having at least a first section and a second section,
    wherein the second section is disposed around the first section and couples the first section to the biocompatible housing, and wherein the first section has a thickness that is greater than a thickness of the second section;
    a vibration sensor disposed in the biocompatible housing and configured to detect vibration of the non-uniform diaphragm and generate signals representative of the vibration; and
    a vibration chamber disposed in the biocompatible housing between the non-uniform diaphragm and the vibration sensor,
    wherein the first section includes a first portion positioned at an inner surface of the non-uniform diaphragm and a second portion positioned at an outer surface of the non-uniform diaphragm, such that the first portion extends from the inner surface into the vibration chamber and the second portion extends from the outer surface away from the vibration chamber.

12. The device of claim 11, further comprising:
    a coupling member configured to mechanically couple the first section of the non-uniform diaphragm to a vibrating structure of a middle ear or an inner ear of a recipient.

13. The device of claim 11, wherein the second section is substantially co-planar with the first section.

14. The device of claim 11, wherein the first section is a central region disposed at a center of the non-uniform diaphragm, wherein the second section is a peripheral region disposed around the central region and coupling the central region to the biocompatible housing.

15. The device of claim 14, wherein the peripheral region has a ring-shape and is disposed around an outer edge of the central region.

16. The device of claim 14, wherein the central region has at least one shape selected from a cylindrical shape and a conical shape.

17. The device of claim 2, wherein the central region has at least one shape selected from a cylindrical shape and a conical shape.

18. A device comprising:
    a biocompatible housing defining a cavity and having an opening at a first end of the biocompatible housing;
    a non-uniform diaphragm attached to the biocompatible housing so as to hermetically seal the opening, the non-uniform diaphragm having at least a first section and a second section, wherein the second section is disposed around the first section and couples the first section to the biocompatible housing, and wherein the first section has a thickness that is greater than a thickness of the second section;

a vibration sensor disposed in the biocompatible housing and configured to detect vibration of the non-uniform diaphragm and generate signals representative of the vibration; and a vibration chamber disposed in the biocompatible housing between the non-uniform diaphragm and the vibration sensor, wherein the first section is positioned at an inner surface of the non-uniform diaphragm such that the first section extends from the inner surface into the vibration chamber.

* * * * *